United States Patent
Okada et al.

(10) Patent No.: US 6,969,771 B2
(45) Date of Patent: Nov. 29, 2005

(54) PROCESS FOR PRODUCING PROCESSED GLYCERIDE FAT

(75) Inventors: Tadayuki Okada, Izumisano (JP); Kotaro Yamaguchi, Tsukuba-gun (JP)

(73) Assignee: Fuji Oil Company, Limited, Osaka (JP)

(*) Notice: Subject to any disclaimer, the term of this patent is extended or adjusted under 35 U.S.C. 154(b) by 16 days.

(21) Appl. No.: 10/480,049

(22) PCT Filed: Jun. 21, 2002

(86) PCT No.: PCT/JP02/06253

§ 371 (c)(1),
(2), (4) Date: Dec. 9, 2003

(87) PCT Pub. No.: WO03/000832

PCT Pub. Date: Jan. 3, 2003

(65) Prior Publication Data

US 2004/0152908 A1   Aug. 5, 2004

(30) Foreign Application Priority Data

Jun. 26, 2001   (JP) .............................. 2001-192743

(51) Int. Cl.⁷ ................................................. C11C 1/00
(52) U.S. Cl. ..................................... 554/169; 435/134
(58) Field of Search ........................ 554/169; 435/134

(56) References Cited

U.S. PATENT DOCUMENTS 4,420,560 A * 12/1983 Matsuo et al. .............. 435/134

FOREIGN PATENT DOCUMENTS

| GB | 2247893 | 3/1992 |
| JP | 62-272982 | 11/1987 |
| JP | 6-62876 | 3/1994 |

* cited by examiner

Primary Examiner—Deborah D. Carr
(74) Attorney, Agent, or Firm—Wenderoth, Lind & Ponack, L.L.P.

(57) ABSTRACT

A process for producing a processed glyceride having a satisfactory color tone and having high purity without the need of a fractionation step, by mitigating the deterioration in a color tone caused by the processing and recycling of a fatty acid ester recovered after an interesterification reaction. The process comprises subjecting a glyceride fat and a fatty acid ester and/or a free fatty acid to interesterification, distilling the reaction product to recover a part or all of fatty acid esters and/or free fatty acids therein, subjecting the distillation fraction recovered to hydrogenation, and to re-distillation or mixing with the fresh fatty acid ester and/or fresh free fatty acid in any order, re-reacting the resultant fraction or mixture with the distillation residue, and separating a fat fraction from the final reaction product, and is characterized in that the content of components other than the fatty acid ester and/or free fatty acid is controlled to 3.0 wt. % or lower.

3 Claims, No Drawings

PROCESS FOR PRODUCING PROCESSED GLYCERIDE FAT

TECHNICAL FIELD

The present invention relates to a process for producing a processed glyceride fat having an excellent color tone and having high purity without the need of a step of fractionating the glyceride fat after an interesterification reaction.

BACKGROUND ART

So far, interesterification has been one of the effective means as a method for modifying fats and oils. As this interesterification, there are a chemical procedure, that is, a metal-catalyzing method of random interesterification using, as a catalyst, a substance such as an alkali metal alcoholate, an alkali metal, an alkali metal hydroxide, or the like, and an enzymatic interesterification method of 1,3-position specific or random interesterification using a lipase.

In such interesterification, since fatty acid esters and/or free fatty acids are produced, they are recovered from the reaction product by distillation after completion of the reaction. Then, they are subjected to processing such as hydrogenation, and recycled as fatty acid esters and/or free fatty acids for interesterification in some cases (JP 3-69516 B). For example, in a process for producing a symmetric triglyceride such as cacao butter by enzymatic interesterification between a fat rich in oleic acid as a constituent fatty acid, and a saturated fatty acid ester and/or a free fatty acid using a lipase, it is advantageous to hydrogenate fatty acid esters and/or free fatty acids containing oleic acid as a main component recovered from the reaction product and recycle them as the aforementioned saturated fatty acid ester and/or free fatty acid.

In interesterification processes, there is also such a reaction manner that an interesterification reaction is performed by a one stage to continuous multi-stage manner in order to obtain a reaction product of a processed glyceride fat having high purity. That is, in this manner, an unreacted fatty acid ester fraction is selectively left in a reaction system after the first stage interesterification reaction, and a fresh unreacted fatty acid ester is added thereto, followed by performing the interesterification reaction of the second stage to obtain a reaction product of the processed glyceride fat having high purity, whereby, a subsequent fractionating step becomes unnecessary (WO 96/10643).

DISCLOSURE OF THE INVENTION

However, according to the present inventors' study, in the aforementioned multi-stage interesterification reaction, it has been found that, when fatty acid esters and/or free fatty acids recovered from a reaction product are subjected to processing and recycling in the interesterification reaction at the second or subsequent stage, there arises such a drawback that a color tone of the processed glyceride fat obtained from the final reaction product is deteriorated.

An object of the present invention is to provide a process for producing a processed glyceride fat having a satisfactory color tone and high purity without causing such drawback and without the need of a step of fractionating the glyceride fat.

As a result of the present inventors' intensively study, the present invention has been completed. The present invention is a process for producing a processed glyceride fat, which comprises subjecting a glyceride fat and a fatty acid ester and/or a free fatty acid to interesterification, distilling the reaction product to recover a part or all of fatty acid esters and/or free fatty acids therein, subjecting the distillation fraction recovered to re-distillation or mixing with the fresh fatty acid ester and/or the fresh free fatty acid, and to hydrogenation, in any order, re-reacting the resultant fraction or mixture with the distillation residue, and separating a glyceride fat fraction from the final reaction product.

Preferably, the content of components other than fatty acid esters and/or free fatty acids in the fraction to be mixed with the distillation residue is reduced to 3.0 wt. % or lower by re-distillation, or mixing with the fresh fatty acid ester and/or the fresh free fatty acid.

BEST MODE FOR CARRYING OUT THE INVENTION

As the raw material glyceride fat to be subjected to interesterification, edible glyceride fats and oils can be widely used, and examples thereof include vegetable fats and oils such as rapeseed oil, soybean oil, sunflower seed oil, cottonseed oil, peanut oil, rice bran oil, corn oil, safflower oil, olive oil, kapok oil, sesame oil, evening prime-rose oil, palm oil, shea butter, sal fat, cacao butter, coconut oil, palm kernel oil and the like, and animal fats and oils such as milk fat, beef tallow, lard, fish oil, whale oil and the like. They can be used alone or in a combination thereof, and also include processed fats and oils obtained by subjecting them to hydrogenation, fractionation, interesterification, or the like. They can be appropriately selected and used according to a particular object. For example, for the purpose of producing hard butter rich in 1,3-di-saturated-di-unsaturated triglyceride (hereinafter, referred to as SUS (S: saturated fatty acid, U: unsaturated fatty acid)) components, a fat in which a large amount of unsaturated fatty acids are bound to the 2-position is preferred is preferable, inter alia, to use a fat rich in oleic acid is more preferable.

Further, as the raw material fatty acid ester and/or free fatty acid, various acyl groups can be used and they may also be appropriately selected and used according to a particular object. Similarly, for the purpose of producing hard butter rich in SUS components, the fatty acid is preferably a saturated fatty acid, inter alia, stearic acid is more preferable. Further, the fatty acid ester is preferably an alcohol ester, particularly, a monohydric lower alcohol ester is more preferable from a viewpoint of the reactivity and the workability.

In the present invention, the interesterification reaction may be any of a reaction by an alkali metal-catalyzing method and a reaction by an enzymatic interesterification method. Preferably, in the present invention, by performing interesterification in a multi-stage manner, a fat having high purity of the objective glyceride fat can be obtained without the need of fractionation. In particular, for the purpose of producing hard butter rich in SUS components, it is advantageous to adopt a multi-stage manner in which, as the first stage, a fatty acid ester and/or a free fatty acid rich in a saturated fatty acid, and a glyceride fat rich in oleic acid at the 2-position are subjected to the interesterification reaction, and a part or all of fatty acid esters and/or free fatty acids in the reaction product are distilled off, when the reaction is completed. Then, after hydrogenation of the resultant distillation fraction, the hydrogenated fraction and the residue of the above distillation are subjected to the interesterification reaction again to obtain the processed glyceride fat having higher purity than that of the fat obtained in the first stage reaction and, if necessary, repeating the reaction again.

The distillation temperature after completion of the reaction at a stage prior to the final stage, i.e., after completion of the reaction of the first stage, the second stage, or the like is as low as possible such as at 200° C. or lower under reduced pressure conditions, more specifically and preferably, at about 170° C. to 180° C. under reduced pressure conditions of 1 to 3 Torr. Further, the distillation for separating the processed glyceride after completion of the reaction at the final stage is preferably performed by, firstly, distillation at about 170° C. to 180° C. under reduced pressure conditions of 1 to 3 Torr, and then, steam distillation at about 230° C. to 240° C. under reduced pressure conditions of 1 to 3 Torr.

In the distillation step at a temperature as low as possible such as at 200° C. or lower under reduced pressure conditions, it is preferable that the recovery of fatty acid esters and/or free fatty acids from the reaction product is usually 50% or more of the fatty acid esters and/or free fatty acids present in the reaction system because, when the amount of remaining unsaturated fatty acid esters coming out by the reaction of the first stage, second stage, or the like becomes larger, the desired purity of the objective processed glyceride fat is hardly obtainable. Further, in the steam distillation step at about 230° C. to 240° C. under reduced pressure conditions, it is preferable to recover almost all of the fatty acid esters and/or free fatty acids.

However, when the interesterification reaction is performed in a multi-stage manner, it is required to perform reaction steps the same number of times as that corresponding to the number of stages as well as the distillation stapes and the steam distillation step. Then, the reactants readily undergo thermal history in respective steps and many by-products are formed in the distillation steps to steam distillation step during the reaction.

When these by-products as well as a distillation fraction of fatty acid esters and/or free fatty acids formed, in particular, a distillation fraction recovered by the steam distillation at 230° C. or higher are hydrogenated and used in the interesterification reaction at a next stage or another interesterification reaction, a deteriorating phenomenon in a color tone of the processed glyceride fat after the final stage reaction may be caused. However, in the present invention, the above deteriorating phenomenon in a color tone can be solved by reducing the content of components other than fatty acid esters and/or free fatty acids in a distillation fraction containing fatty acid esters and/or free fatty acids recovered from the reaction product by re-distillation or mixing with the fresh fatty acid ester and/or the fresh free fatty acid, preferably by controlling the content to 3.0 wt. % or lower.

As aspects of reducing the content of components other than fatty acid esters and/or free fatty acids, there are methods:

(1) wherein fatty acid esters and/or fatty acids distilled from the reaction product by steam distillation at about 230° C. or higher at the final stage is mixed and combined with the fatty acid ester and/or-free fatty acid scarcely containing impurities such as a commercially available reagent, or the like, or with the fresh fatty acid ester and/or fresh free fatty acid which has never undergone a reaction step and does not contain an increased amount of impurities such as unsaponifiable matter so that the content of components other than fatty acid esters and/or free fatty acids is 3.0 wt. % or lower;

(2) wherein fatty acid esters and/or free fatty acids distilled from a reaction product by distillation at about 200° C. or lower at any stage up to that prior to the final stage are used in an large amount, fatty acid esters and/or free fatty acids distilled from a reaction product by steam distillation at about 230° C. at the final stage are used in a small amount, and they are mixed and combined so that the content of components other than fatty acid esters and/or free fatty acids is 3.0 wt. % or lower; or (3) wherein only fatty acid esters and/or free fatty acids distilled from the reaction product by steam distillation at about 230° C. or higher at the final stage, or a mixture obtained by mixing and combining fatty acid esters and/or free fatty acids distilled from a reaction product by distillation at about 200° C. or lower at any stage up to that prior to the final stage with fatty acid esters and/or free fatty acids distilled from the reaction product by steam distillation at about 230° C. or higher at the final stage at an arbitrary ratio are(is) subjected to re-distillation treatment at about 200° C. to 210° C. under reduced pressures of 1 to 3 Torr, so that the content of components other than fatty acid esters and/or free fatty acids in the fatty acid esters and/or the free fatty acids is 3.0 wt. % or lower; and the like.

These steps for reducing components other than fatty acid esters and/or free fatty acids can be performed in combination with hydrogenation in any order, followed by subjecting to the re-reaction with a distillation residue at any stage up to that prior to the final stage. The hydrogenation step of fatty acid esters and/or fatty acids for recycling is preferably maximum hydrogenation in order to obtain the processed glyceride fat having high purity. In addition, regarding the fatty acid ester and/or free fatty acid containing no impurities such as a commercially available reagent, or the like, or the fresh fatty acid ester and/or the fresh free fatty acid which has never undergone a reaction step, maximum hydrogenation is also preferable.

In conversion of triglycerides by an enzymatic interesterification reaction of fats and oils, a fatty acid ester and/or a free fatty acid are used together, and, in this reaction system, triglycerides (TG), diglycerides (DG), water (H$_2$O) and free fatty acids (FA) are present in an equilibrium state as follows:

$$TG+H_2O=DG+FA$$

Here, the larger the amount of FA present is, the more the hydrolysis reaction toward the right direction for formation of FA is suppressed. Therefore, when a free fatty acid is added to an interesterification reaction system between a fat and a fatty acid ester, the hydrolysis reaction is suppressed, and the production of diglycerides, consequently, the production of SSA can be suppressed upon production of hard butter rich in SUS components without reduction of a reaction rate and without the need of a solvent.

In the present invention, the higher an acid value indicating an amount of a free fatty acid fraction present in fatty acid esters and/or the free fatty acids to be recycled is, the more the advantages of the present invention are enhanced. However, when the acid value exceeds 30, a rate of the interesterification reaction which is the main reaction is reduced and a conversion rate of the objective triglyceride is remarkably decreased. In addition, crystals of free fatty acids are apt to be precipitated. For preventing this, it is required to raise a reaction temperature to around 60° C. However, a reaction under such a high temperature generally accelerates inactivation of an enzyme, and is undesired. Therefore, preferably, the acid value of fatty acid esters and/or free fatty acids is 30 or less, in particular, 20 or less.

In addition, when the acid value is less than 8, the effect of suppressing hydrolysis is scarcely observed. Therefore, preferably, the acid value of fatty acid esters and/or free fatty acids is 8 or more and, in particular, when the interesterification reaction is performed at a multi-stage, the acid value is preferably 10 or more.

The content of components other than fatty acid esters and/or free fatty acids in the fatty acid ester and/or free fatty acid fraction corresponds to the content (%) of unsaponifiable matter. The amounts other than the amount of fatty acid esters and/or free fatty acids referred to in Examples hereinafter are those measured in terms of the content of unsaponifiable matter. More specifically, according to A.O.C.S. Official Method Ca 6a-40 Unsaponifiable Matter, the procedures up to Procedure 7 are performed to obtain unsaponifiable matter, this is diluted 10-fold with carbon tetrachloride, 0.5 to 0.7 μl of the dilution is injected into gas chromatography (gas chromatography procedural conditions are shown hereinafter), the content of fatty acid contaminant in the unsaponifiable matter is calculated from the resulting quantitative analysis value, and the content of unsaponifiable matter can be calculated by the following equation.

Content of unsaponifiable matter (%)=weight of unsaponifiable matter (g)×(100−content of fatty acids contaminant in unsaponifiable matters (%)) ÷weight of sample used (g).

Gas chromatography procedural conditions (Shimadzu GC-7A)
Injection Temp: 350° C.
Column Temp: 150° C.→350° C. (4° C./min)
10 min hold
Column: 0.5 m×2.3 mm
Liquid phase: Silicon OV-17 1.5%
Support: Shimalite W (AW-DMCS)
Director: FID
Carrier gas: N2

The distillation residue in the present invention is a residue obtained by, after the enzymatic interesterification reaction between the raw material glyceride fat and the raw material fatty acid ester and/or free fatty acid, distilling a reaction product to remove and recover a part or all of fatty acid esters and/or free fatty acids therefrom. Thus, SUS components of the objective processed glyceride fat are concentrated therein. The amount of SUS components of the processed glyceride fat in the distillation residue after aforementioned one stage interesterification reaction between a stearic acid ester and a glyceride fat rich in oleic acid is 40 to 50 wt. %.

The re-reaction at the second or subsequent stage can be performed by mixing and combining the distilled residue and the fatty acid esters and/or free fatty acids at, usually, the same ratio as that of the reaction substrate of the first stage. However, the mixing and combining ratio of the distilled residue and fatty acid esters and/or free fatty acids may be changed depending on purity of the objective final processed glyceride fat.

For separating the glyceride fat fraction from the final reaction product, it is preferable that, after the final stage interesterification reaction, fatty acid esters and/or free fatty acids are distilled off by distillation at about 170° C. to 180° C. under reduced pressure conditions of 1 to 3 Torr, followed by steam distillation purification at about 230° C. to 240° C. under reduced pressure conditions of 1 to 3 Torr to remove monoglycerides (MG), diglycerides (DG) and unsaponifiable matter which produced by the interesterification reaction, as well as fatty acid esters and/or free fatty acids remained without being distilled off at about 170° C. to 180° C. under reduced pressure conditions of 1 to 3 Torr.

The processed glyceride fat is typically hard butter rich in SUS components and, at this time, the preferred content of SUS components is 50 wt. % or more, desirably 60 wt. % or more. Therefore, a fractionation step is not required. According to the present invention, hard butter of good quality which has the contents of DG components and SSS components of 5.0 wt. % or less, and 4.0 wt. % or less, desirably 3.0 wt. % or less and 2.5 wt. % or less, respectively, can be obtained.

EXAMPLES

Hereinafter, embodiments of the present invention will be illustrated by Examples, but these Examples are merely exemplification, and the spirit of the present invention is not limited by these Examples. In Examples, both of parts and percents are by weight.

Example 1

(1) Preparation of Re-distilled Ethyl Stearate

A mixed oil obtained by mixing 80 parts of commercially available ethyl stearate and 20 parts of a high oleic sunflower deacidified oil was heated at 110° C. under reduced pressure to dehydrate the mixture until the moisture content became 70 ppm. The dehydrated reaction substrate was passed through a column packed with 120 g of diatomaceous earth carrying a lipase (originated from *Rhizopus nibeus*) having 1,3-specificity at 40° C. and at a flow rate of 50 g/hr to perform an interesterification reaction. A reaction product was finally recovered from the reaction oil at 230° C. for 90 minutes under reduced pressure conditions of 2 Torr, from which fatty acid esters and/or free fatty acids were obtained and subjected to maximum hydrogenation. The content of components other than fatty acid esters and/or free fatty acids was 4.1 wt. %. A portion of this was distilled at 210° C. under reduced pressure conditions of 2 Torr to prepare re-distilled ethyl stearate from which fatty acid ester and/or free fatty acid components other than fatty acid esters and/or free fatty acids were removed. The content of components other than fatty acid esters and/or free fatty acids in the re-distilled fatty acid esters and/or free fatty acids was 1.9 wt. %. The acid value of fatty acid esters and/or free fatty acids was adjusted to 15.

(2) Preparation of Interesterification Reaction Fat

A mixed oil obtained by mixing 80 parts of the re-distilled fatty acid esters and/or free fatty acids prepared in (1) and 20 parts of a deacidified high oleic sunflower oil was heated at 110° C. under reduced pressure to dehydrate the mixture until the moisture content became 70 ppm. Then, the above reaction substrate was passed through a column packed with 120 g of diatomaceous earth carrying lipase (originated from Rhizopus nibeus) having the 1,3-specificity and interesterification activating at 40° C. and at a flow rate of 50 g/hr to perform an interesterification reaction. The resulting interesterification reaction oil was subjected to purification distillation at 170° C. to 180° C. under reduced pressure conditions of 2 Torr to distill off a portion of fatty acid esters (71.3 wt. %) mainly combining oleic acid from the reaction product to obtain a distillation residue in which the interesterification reaction fat was concentrated. Then, this concentrated interesterification reaction fat was mixed with the re-distilled fatty acid esters and/or free fatty acids prepared in (1), and the mixture was adjusted so that glyceride fat:fatty acid esters and/or free fatty acid became 20 parts:80 parts. Similarly, dehydration treatment was performed, and the interesterification reaction through the column was performed again and, thereafter, the resulting interesterification reaction oil was treated at 170° C. to 180° C. under reduced pressure conditions of 2 Torr to distill off fatty acid esters combining oleic acid from the reaction product. Then, steam distillation purification was performed at about 230° C. to 240° C. under reduced pressure conditions of 2 Torr to obtain the final proceeded glyceride fat. The content of components other than fatty acid esters and/or free fatty acids in the fatty acid esters and/or free fatty aids which had been recycled in the reaction was 1.9 wt. %. Thus obtained interesterification reaction fat was decolored and deodorized according to a conventional method, and the color tone thereof was measured by Lovibond method (prescribed by Japan Oil Chemistry Society Standard Fat Analysis Test Method 2.2.1.1.-1996). As a result, R was 0.8 and Y was 4.8. The quality of the final processed glyceride fat was SUS components: 81.5 wt. %, DG components: 2.7 wt. %, SSS components: 2.3 wt. %.

Example 2

A part of the fatty acid esters and/or free fatty acids (the content of components other than fatty acid esters and/or free fatty acids in the fatty acid esters and/or free fatty acids was 4.1 wt. %) from the reaction product obtained in Example 1 was distilled at 210° C. under reduced pressure conditions of 2 Torr to obtain the re-distilled fatty acid esters and/or free fatty acids (the content of components other than fatty acid esters and/or free fatty acids in the re-distilled fatty acid esters and/or free fatty acids was 2.8 wt. %), and the acid value thereof was adjusted to 15 to obtain the final processed glyceride fat under the same conditions as those of Example 1. As a result, a color tone was R: 1.3, Y: 7.1. The quality of the final processed glyceride fat was SUS components: 81.3 wt. %, DG components: 2.8 wt. %, SSS components: 2.4 wt. %.

Similarly, the content of components other than fatty acid esters and/or free fatty acids in the fatty acid esters and/or free fatty acids was controlled to 3.3 wt. %, and the acid value was adjusted to 15 to obtain the final processed glyceride under the same conditions as those of Example1. The fat had R: 6.1, Y: 58.0. Thus, it has been found that a color tone is significantly improved by controlling the content of components other than fatty acid esters and/or free fatty acids in the fatty acid esters and/or free fatty acids to 3.0 wt. % or lower. At this time, the quality of the final processed glyceride fat was SUS components: 80.8 wt. %, DG components: 2.8 wt. %, SSS components: 2.3 wt. %.

Commercially available stearic acid ester (trade name "Ethyl Stearate (guaranteed)" manufactured by Inoue Koryo Seizosho Co., Ltd.) and stearic acid (trade name "Stearic Acid (guaranteed)" manufactured by Wako Pure Chemical Industries, Ltd.) were mixed and combined, the acid value was adjusted to 15 (components other than fatty acid esters and/or free fatty acids were not detected), the same distilled residue as that obtained in Example 1 was used and the final processed glyceride fat was obtained under the same conditions as those of Example 1. As a result, a color tone was R: 0.4, Y:4.1. The quality of the final processed glyceride fat was SUS components: 81.7 wt. %, DG: components 2.5 wt. %, SSS components: 2.2 wt. %.

Comparative Example 1

According to the same manner as that of Example 1, the processed glyceride fat was obtained except that fatty acid esters and/or free fatty acids from the reaction product in (1) were used without re-distillation. As a result, a color tone was R: 11.0, Y: 79.9. The quality of the final processed glyceride fat was SUS components: 80.2 wt. %, DG components: 2.9 wt. %, SSS components: 2.4 wt. %.

In view of the above results, in Examples 1 and 2 in which the re-distilled fatty acid esters and/or free fatty acids recovered from the reaction product by distillation were used as the fatty acid esters and/or free fatty acids to be recycled, a color tone of the interesterification reaction fat is significantly improved as compared with that of Comparative Example 1 in which re-distillation is not performed. Thus, even when re-distillation is performed, an significant advantage can be obtained by controlling the content of components other than fatty acid esters and/or free fatty acids in the fatty acid esters and/or free fatty acids to 3.0 wt. % or lower.

INDUSTRIAL APPLICABILITY

As described above, in a process for producing a processed glyceride fat which comprises subjecting a glyceride fat and a fatty acid ester and/or a free fatty acid to interesterification, distilling the reaction product to recover a part or all of fatty acid esters and/or free fatty acids therein, subjecting the distillation fraction recovered to hydrogenation, and to re-distillation or mixing with the fresh fatty acid ester and/or the fresh free fatty acid in any order, re-reacting the resultant fraction or mixture with the distillation residue, and separating the glyceride fat fraction from the final reaction product, such an excellent advantage that the processed glyceride fat having high purity and a significantly improved color tone is obtained, can be exerted without the need of fractionation by reducing the content of components other than fatty acid esters and/or free fatty acids in the fatty acid esters and/or free fatty acids to control the content, preferably, at 3.0 wt. % or lower.

What is claimed is:

1. A process for producing a processed glyceride fat, which comprises subjecting a glyceride fat and a fatty acid ester and/or a free fatty acid to interesterification, distilling the reaction product to recover a part or all of fatty acid esters and/or free fatty acids therein, subjecting the distillation fraction recovered to re-distillation or mixing with the fresh fatty acid ester and/or the fresh free fatty acid, and to hydrogenation, in any order, re-reacting the resultant fraction or mixture with the distillation residue, and separating the glyceride fat fraction from the final reaction product.

2. The process for producing a processed glyceride fat according to claim 1, wherein the content of components other than fatty acid esters and/or free fatty acids in a fraction to be mixed with the distillation residue is reduced to 3.0 wt. % or lower by re-distillation or mixing with the fresh fatty acid ester and/or the fresh free fatty acid.

3. The process for producing a processed glyceride fat according to claim 1, wherein the processed glyceride fat is hard butter, the 2-position of a raw material glyceride fat is rich in an unsaturated constituent fatty acid, a raw material fatty acid ester and/or free fatty acid are rich in a saturated fatty acid ester or a saturated fatty acid, and interesterification is a 1,3-position specific reaction.

* * * * *